United States Patent [19]

Köppe et al.

[11] 3,975,539

[45] Aug. 17, 1976

[54] PHARMACEUTICAL COMPOSITIONS CONTAINING AN N,N-BIS-(3-PHENOXY-2-HYDROXY-PROPYL)-ALKYLENEDIAMINE AND METHOD OF USE

[75] Inventors: Herbert Köppe; Helmut Stähle; Werner Kummer; Gojko Muacevic; Werner Traunecker, all of Ingelheim am Rhein, Germany

[73] Assignee: Boehringer Ingelheim GmbH, Ingelheim am Rhein, Germany

[22] Filed: Apr. 16, 1975

[21] Appl. No.: 568,798

Related U.S. Application Data

[62] Division of Ser. No. 336,269, Feb. 27, 1973, Pat. No. 3,888,898.

[30] Foreign Application Priority Data

Mar. 6, 1972 Germany............................ 2210620
Dec. 11, 1972 Germany............................ 2260444

[52] U.S. Cl................................ 424/304; 424/330
[51] Int. Cl.²...................................... A61K 31/275
[58] Field of Search................. 424/304; 260/465 E

[56] References Cited

UNITED STATES PATENTS

| | | | |
|---|---|---|---|
| 3,644,469 | 2/1972 | Koppe et al. | 424/304 |
| 3,644,636 | 2/1972 | Koppe et al. | 424/304 |
| 3,836,671 | 9/1974 | Barrett et al. | 424/304 |
| 3,888,898 | 6/1975 | Koppe et al. | 424/304 |

*Primary Examiner*—V. D. Turner
*Attorney, Agent, or Firm*—Hammond & Littell

[57] ABSTRACT

Pharmaceutical compositions containing as an active ingredient a compound of the formula

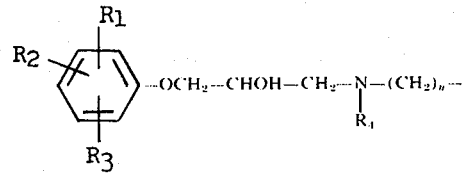

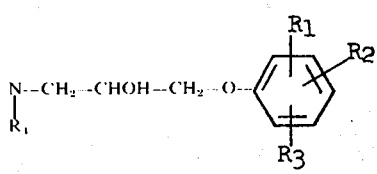

wherein
 $R_1$ is $-(CH_2)_x-CN$, where $x$ is 0,1,2 or 3,
 $R_2$ is hydrogen, halogen, alkyl of 1 to 5 carbon atoms, alkoxy of 1 to 5 carbon atoms, alkenyl of 2 to 5 carbon atoms or alkenyloxy of 2 to 5 carbon atoms;
 $R_3$ is hydrogen, halogen, alkyl of 1 to 5 carbon atoms or alkoxy of 1 to 5 carbon atoms;
 $R_2$ and $R_3$, together with each other and the carbon atoms to which they are attached, form a saturated or unsaturated carbocyclic ring of up to 6 carbon atoms;
 $R_4$ is hydrogen, alkyl of 1 to 5 carbon atoms or aralkyl; and
 $n$ is an integer from 1 to 10, inclusive; or a non-toxic, pharmacologically acceptable acid addition salt thereof; and a method of using the same as $\beta$-adrenergic receptor blockers and hypotensives.

6 Claims, No Drawings

PHARMACEUTICAL COMPOSITIONS CONTAINING AN N,N-BIS-(3-PHENOXY-2-HYDROXY-PROPYL)-ALKYLENEDIAMINE AND METHOD OF USE

This is a division of copending application Ser. No. 336,269, filed Feb. 27, 1973, now U.S. Pat. No. 3,888,898 granted June 10, 1975.

This invention relates to novel pharmaceutical compositions containing an N,N'-bis-(3-phenoxy-2-hydroxy-n-propyl)-alkylenediamine or a salt thereof, as well as to a method of using the same as $\beta$-adrenergic receptor blocking agents and hypotensives.

More particularly, the present invention relates to pharmaceutical dosage unit compositions containing as an active ingredient a compound of the formula

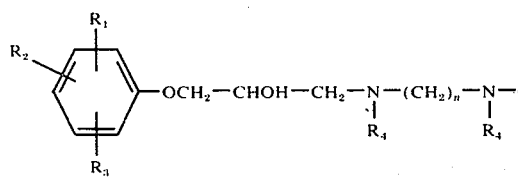
(I)

wherein
- $R_1$ is -$(CH_2)_x$-CN, where x is 0,1,2 or 3,
- $R_2$ is hydrogen, halogen, alkyl of 1 to 5 carbon atoms, alkoxy of 1 to 5 carbon atoms, alkenyl of 2 to 5 carbon atoms or alkenyloxy of 2 to 5 carbon atoms;
- $R_3$ is hydrogen, halogen, alkyl of 1 to 5 carbon atoms or alkoxy of 1 to 5 carbon atoms;
- $R_2$ and $R_3$, together with each other and the carbon atoms to which they are attached, form a saturated or unsaturated carbocyclic ring of up to 6 carbon atoms;
- $R_4$ is hydrogen, alkyl of 1 to 5 carbon atoms or aralkyl; and
- $n$ is an integer from 1 to 10, inclusive;

or a non-toxic, pharmacologically acceptable acid addition salt thereof.

Particularly preferred embodiments of the compositions according to the present invention are those wherein the active ingredient is a compound of the formula

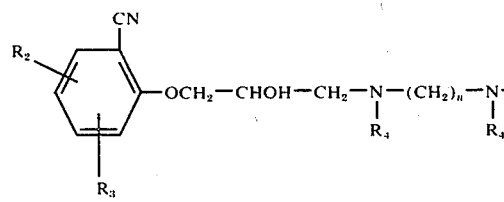
(Ia)

wherein
- $R_2$ is hydrogen, halogen, alkyl of 1 to 5 carbon atoms, alkoxy of 1 to 5 carbon atoms, alkenyl of 2 to 5 carbon atoms or alkenyloxy of 2 to 5 carbon atoms;
- $R_3$ is hydrogen, halogen, alkyl of 1 to 5 carbon atoms or alkoxy of 1 to 5 carbon atoms;
- $R_2$ and $R_3$, together with each other and the carbon atoms to which they are attached, form a saturated or unsaturated carbocyclic ring of up to 6 carbon atoms;
- $R_4$ is hydrogen, alkyl of 1 to 5 carbon atoms or aralkyl; and
- $n$ is an integer from 1 to 10, inclusive;

or a non-toxic, pharmacologically acceptable acid addition salt thereof.

The compounds embraced by formula I above may be prepared by the following methods:

Method A

By reacting a compound of the formula

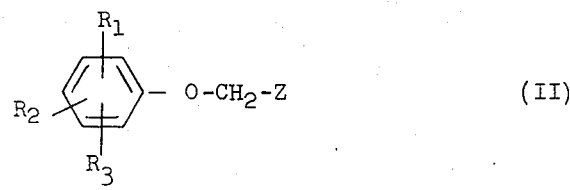
(II)

wherein $R_1$ to $R_3$ have the meanings defined above, and Z is

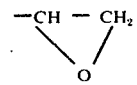

or

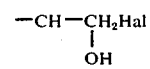

(Hal = halogen), with an alkylenediamine of the formula $$R_4HN-(CH_2)_n-NHR_4 \qquad (III)$$

wherein $R_4$ and $n$ have the meanings defined above.

Method B

By reacting a compound of the formula

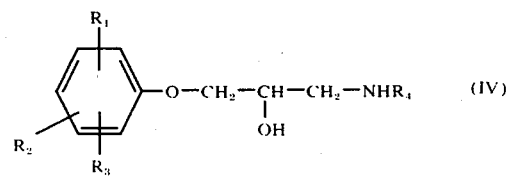
(IV)

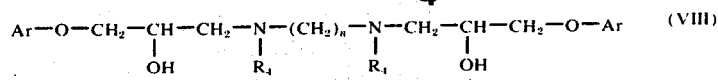

wherein $R_1$ to $R_4$ have the meanings previously defined, with an alkylenedihalide of the formula $$\text{Hal-(CH}_2)_n\text{-Hal} \quad (V)$$

wherein $n$ and Hal have the above-defined meanings. The reaction proceeds in 2 steps with intermediate formation of a compound of the formula

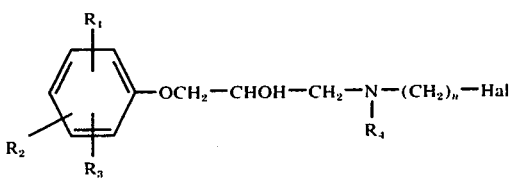
(VI)

wherein $R_1$ to $R_4$, $n$ and Hal have the meanings defined above. It is also possible to produce a compound of the formula I directly from a compound of the formula VI by reacting it with a compound of the formula IV.

Method C

By alkylating a compound of the formula

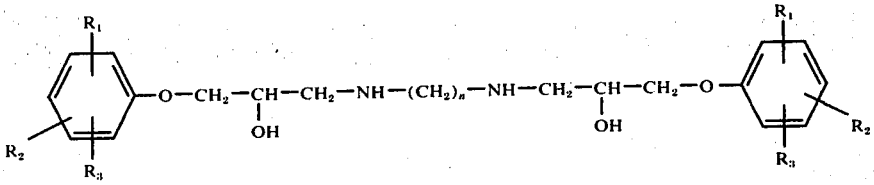
(VII)

wherein $R_1$ to $R_3$ and $n$ have the above defined meanings, for example, with an electrophilic compound of the formula $R_4$-X, wherein $R_4$ has the meaning previously defined and X is an anionically easily removable group, such as halogen or alkyl- or aryl-sulfonyl, or with an aliphatic ketone corresponding to radical $R_4$ under reducing conditions.

Further methods for producing the compounds of the formula I include, for example, converting a starting compound wherein the bis-(aryloxypropanolamine)-alkylene structure is already present, but one of the substituents, such as —CN, is still missing or only present in the form of a precursor, into a compound of the formula I by introducing the missing substituent or by converting the precursor of the substituent into the substituent —CN.

For example, the following method is illustrative thereof.

Method D

A compound of the formula

(VIII)

wherein $R_4$ and $n$ have the previously defined meanings and Ar is

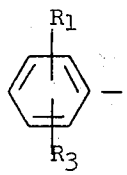
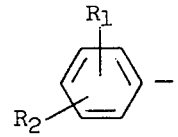

whereby $R_1$, $R_2$ and $R_3$ have the previously defined meanings, may be halogenated by reacting it with chlorine or bromine in acetic acid or with a mixture of hydrogen peroxide and the corresponding hydrohalic acid at elevated temperature.

It is further possible to prepare a compound of the formula I by:

Method E

Reacting a compound of the formula

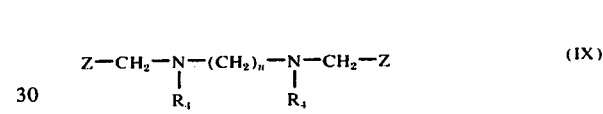
(IX)

wherein $R_4$, $n$ and Z have the previously defined meanings, with a phenol of the formula

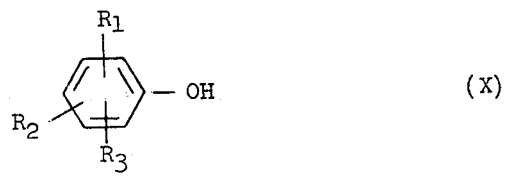
(X)

wherein $R_1$ to $R_3$ have the previously defined meanings, or with a salt thereof. This method is primarily suitable for the preparation of a compound of the formula I wherein $R_4$ is alkyl.

Most of the starting compounds of the formulas II to X are known. Those which are not known may be prepared by conventional methods. Thus, an epoxide of the formula II may be obtained by reacting the corresponding phenol of the formula I or a salt thereof (preferably an alkali metal salt) with epichlorohydrin; a halohydrin of the formula II may be obtained by cleavage of the epoxide with the corresponding hydrohalic acid.

A compound of the formula III wherein $R_4$ is alkyl may be obtained from the corresponding compound of the formula III wherein $R_4$ is hydrogen, by treatment with a conventional alkylating agent $R_4$-X (X = radical of a reactive ester, such as halogen or toluenesulfonyloxy). Secondary alkyl groups may also be obtained by reductive amination with the corresponding ketone, such as acetone, and $NaBH_4$.

A compound of the formula IV may be obtained by reacting a compound of the formula II with an amine of the formula $NH_2$-$R_4$, where $R_4$ has the meanings defined above.

A compound of the formula V is obtainable from a corresponding dialcohol HO-$(CH_2)_n$-OH by reaction with a conventional halogenating agent, such as $SOCl_2$ or $PCl_5$.

A compound of the formula VI may be prepared by reacting a corresponding haloalkylamine of the formula $$R_4NH\text{-}(CH_2)_n\text{-}Hal \qquad (XI)$$

wherein $R_4$, $n$ and Hal have the previously defined meanings, with a compound of the formula II.

The compounds of the formula VII and VIII already contain the bis-(aryloxypropanolamine)-alkylene structure; therefore, they may be obtained with the aid of method B, where substitution of the phenyl moieties of the compound of the formula II has to correspond to that of the desired intermediate product of the formulas VII and VIII.

A compound of the formula IX may be obtained from a compound of the formula III by reacting the latter with epichlorohydrin. A halohydrin of the formula IX thus obtained may be converted into an epoxide of the formula IX by means of aqueous sodium hydroxide.

The compounds embraced by formula I possess two asymmetric carbon atoms and occur therefore as racemates, as well as in the form of optical antipodes. The racemates may be separated with the aid of optically active auxiliary acids, such as di-0,0-p-toluyl-D-tartaric acid, into their optical antipode components.

The compounds of the formula I, both in the form of racemates or optical antipodes, form acid addition salts with inorganic or organic acids. Examples of non-toxic, pharmacologically acceptable acid addition salts are those formed with hydrochloric acid, hydrobromic acid, sulfuric acid, maleic acid, lactic acid, methanesulfonic acid, oxalic acid, tartaric acid, 8-chlorotheophylline or the like.

The following examples illustrate the preparation of compounds of the formula I and salts thereof.

EXAMPLE 1

N,N'-bis-[2'-hydroxy-3'-(2''-cyano-phenoxy)-1-propyl]-1,4-diamino-butane . 2 HCl by method A 20 gm (0.114 mol) of 1-( 2'-cyano-phenoxy)-2,3-epoxy-propane and 3.7 gm (0.042 mol) of 1,4-diamino-butane were refluxed in 100 ml of methanol for 2 hours. After having distilled off the methanol, the residue was dissolved in ethanol and acidified with ethereal HCl. The precipitated crystalline substance was recrystallized from methanol, yielding 3.5 gm of the compound of the formula

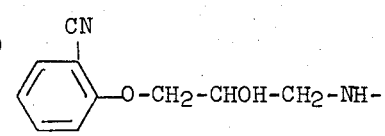

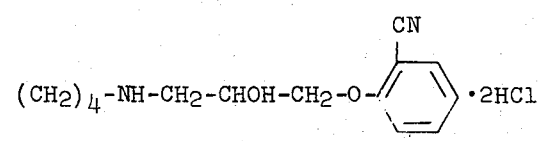

which had a melting point of 227°–228°C.

EXAMPLE 2

N,N'-bis-[2'-hydroxy-3'-(2''-cyano-phenoxy)-1'-propyl]-1,6-hexamethylenediamine . 2 HCl by method A 87.5 gm (0.5 mol) of 1-(2'-cyano-phenoxy)-2,3-epoxy-propane were refluxed with 29 gm (0.25 mol) of hexamethylene-diamine in 750 ml of methanol for 3 hours. After having distilled off the solvent, the residue was treated with about 700 ml of dilute HCl, and insoluble matter was separated. The aqueous phase fractionally made alkaline with NaOH, and the basic fractions precipitating between pH 7.5 and 8.5 were taken up in ether and washed with water. After drying and distilling off the ether, 16 gm of the free base remained behind, which were dissolved in methanol and acidified with alcoholic HCl. Upon addition of ether, 9 gm of the analytically pure hydrochloride, m.p. 200°–203°C., crystallized out.

Analogous to Example 1 (method A) the following additional compounds of the formula I were prepared from the correspondong epoxide of the formula II and the corresponding alkylenediamine of the formula III.

TABLE

| Example No. | $R_1$ | $R_2$ | n | m.p. of hydrochloride |
|---|---|---|---|---|
| 3 | 2-CN | H | 2 | 212–215°C. |
| 4 | 2-CN | H | 8 | 193–195°C. |
| 5 | 2-CN | H | 9 | 182–185°C. |
| 6 | 2-CN | H | 5 | 202–204°C. |
| 7 | 2-CN | H | 3 | 219–220°C. |

TABLE-continued

| Example No. | $R_1$ | $R_2$ | n | m.p. of hydrochloride |
|---|---|---|---|---|
| 8 | 2-CN | H | 7 | 187–190°C. |
| 9 | 2-CN | 5-CH$_3$ | 6 | 206–209°C. |
| 10 | 4-CN | H | 6 | 210–211°C. |
| 11 | 2-OCH$_3$ | 4-CN | 6 | 178–182°C. |
| 12 | 2,4-di-Cl | 6-CN | 5 | |

EXAMPLE 13

N,N'-bis-isopropyl-N,N'-bis[2'-hydroxy-3'-(2''-cyano-phenoxy)-1'-propyl]-1,6-hexamethylenediamine . 2 HCl by method B 11.7 gm (0.05 mol) of 1-(2'-cyano-phenoxy)-3-isopropylamino-2-propanol were refluxed with 6.1 gm (0.025 mol) of 1,6-dibromohexane in 80 ml of ethanol in the presence of 5 gm (0.06 mol) of NaHCO$_3$ for 20 hours. Thereafter, the solvent was distilled off, the residue was digested with dilute NaOH, and the basic components were taken up in CHCl$_3$. The organic phase was washed with water and dried over Na$_2$SO$_4$. After having distilled off the CHCl$_3$, the viscous residue was purified by column-chromatography. The base was dissolved in a little ethanol, and ethereal HCl was added. The hydrochloride crystallized out in the form of colorless crystals after addition of ether. Yield: 4.5 gm; m.p. 189°–192°C.

EXAMPLE 14

N,N'-Bis-methyl-N,N'-bis-[2'-hydroxy-3'-(2''-cyano-phenoxy)-1'-propyl]-1,2-ethylenediamine dioxalate by method C A mixture consisting of 4.1 gm (0.01 mol) of N,N'-bis-[2'-hydroxy-3'-(2''-cyano-phenoxy)-1'-propyl]-1,2-ethylenediamine, 100 ml of CH$_3$OH, 2.8 gm of CH$_3$I (0.022 mol) and 4 gm of NaHCO$_3$ was heated a its boiling point for 3 hours. Thereafer the solvent was distilled off, the residue was digested with dilute NaOH, the base was extracted with CHCl$_3$, and the organic phase was washed with H$_2$O and dried over MgSO$_4$. After distilling off the CHCl$_3$, the residue was purifed by column-chromatography. The fraction containing the pure diamine was evaporated in vacuo, the residue was dissolved in a little methanol, and a solution of oxalic acid in acetone was added. The colorless substance which crystallized out after a short time (1.2 gm) was identified to be the compound of the formula

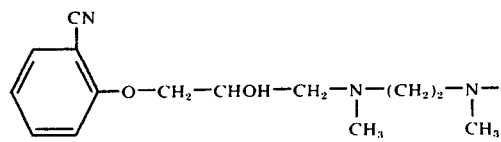

having a melting point of 152°–154°C.

EXAMPLE 15

N,N'-Bis-[2'-hydroxy-3'-(2''-cyano-4'',6''-dichloro-phenoxy)-1'-propyl]-1,5-pentamethylenediamine . 2 HCl by method D 4.52 gm (0.01 mol) of N,N'-bis-[2'-hydroxy-3'-(2''-cyano-phenoxy)- 1'-propyl]-1,5-pentamethylenediamine were dissolved in 50 ml of conc. HCl, and the solution was heated to 40°C. While stirring, 2.42 gm of water were added dropwise, whereby the temperature rose to about 60°C. After one hour the reaction mixture was cooled, evaporated in vacuo, and the residue, after extraction with ether, was made alkaline with NaOH. The basic components were taken up in CHCl$_3$, and the organic phase was washed with H$_2$O and dried over MgSO$_4$. The CHCl$_3$ was distilled off, and the residual mixture of bases was column-chromatographically purified. The diamine was dissolved in a little ethanol, and ethereal HCl was added, whereby a colorless substance crystallized out, yielding 0.8 gm of the compound of the formula

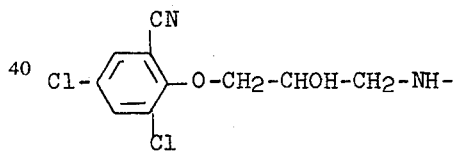

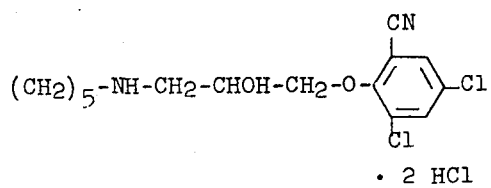

· 2 HCl

EXAMPLE 16

N,N'-bis-[1'-(2''-cyano-phenoxy)-2'-hydroxy-propyl-3']-propylene-1,3-diamine by method E 9.25 gm (0.01 mol) of epichlorohydrin were dis-

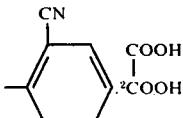

solved in 50 ml of ethanol, a solution of 3.7 gm of propylene-1,3-diamine in 30 ml of ethanol was added, and the mixture was heated at 55°C. for 2 hours, while stirring. Then, the solvent was distilled off, and the residue was purified on a silicagel column. 4.2 gm (0.02 mol) of the isolated N,N'-bis-(2'-hydroxy-3'-chloropropyl-1')-propylene-1,3-diamine were dissolved in 20 ml of methanol, and the solution was added dropwise to a solution of 4.8 gm (0.04 mol) of 2-cyano-phenol and 2.2 gm of KOH (0.04 mol) in 30 ml of methanol, while stirring. Then, the mixture was refluxed for six hours. After distilling off the solvent, the reaction mixture was separated on a silicagel column. The fractions containing the desired compound were combined, the mixture of solvents was distilled off, the residue was dissolved in a little ethanol, and ethereal HCl was added. The precipitated colorless crystals had a melting point of 217°–220°C. and were identified to be the compound of the formula

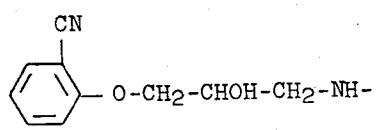

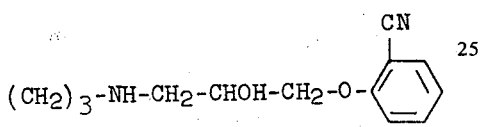

The compounds embraced by formula I and their non-toxic, pharmacologically acceptable acid addition salts have useful pharmacodynamic properties. More particularly, the compounds of the present invention exhibit β-adrenergic receptor blocking and hypotensive activities in warm-blooded animals, such as guinea pigs, cats and dogs.

Of particular significance is the cardio-selective blocking action upon the β-receptors of the heart, i.e. the so-called $\beta_1$-activity, which the compounds according to the present invention produce.

Therefore, the compounds embraced by formula I and their non-toxic, pharmacologically acceptable acid addition salts are useful for the treatment of prophylaxis of disorders of the heart or coronary vessels as well as hypertension in warm-blooded animals.

Especially effective are N,N'-bis-[2'-hydroxy-3'-(2''-cyano-phenoxy)-1'-n-propyl]-1,6-hexamethylenediamine and its non-toxic, pharmacologically acceptable acid addition salts, for example.

For pharmaceutical purposes the compounds of the formula I are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. The effective single dosage unit range of the compounds is from 0.0016 to 5.0 mgm/kg body weight. The preferred oral dosage unit range is 0.016 to 1.0 mgm/kg body weight, and the preferred parenteral dosage unit range is 0.0016 to 0.5 mgm/kg body weight.

The following examples illustrate a few pharmaceutical dosage unit compositions comprising a compound of the formula I as an active ingredient and represent the best modes contemplated of putting the invention into practical use. The parts by weight unless otherwise specified.

EXAMPLE 17

Tablets

The tablet composition is compounded from the following ingredients:

| | |
|---|---|
| N,N'-bis-[2'-hydroxy-3'-(2''cyano-phenoxy)-1'-propyl]-1,2-ethylenediamine.2 HCl | 20.0 parts |
| Corn starch | 164.0 parts |
| Calcium phosphate | 240.0 parts |
| Magnesium stearate | 1.0 parts |
| | 425.0 parts |

Preparation:

The individual ingredients are intimately admixed with each other, and the mixture is granulated in the conventional way. Then, the granulate is compressed into 425 mgm-tablets each of which contains 20 mgm of the ethylenediamine compound and is an oral dosage unit composition with effective β-adrenergic receptor blocking and hypotensive action.

EXAMPLE 18

Gelatin Capsules

The capsule filler composition is compounded from the following ingredients:

| | |
|---|---|
| N,N'-bis-[2'-hydroxy-3'-(2''-cyano-phenoxy)-1'-propyl]-1,6-hexamethylenediamine . 2 HCl | 25.0 parts |
| Corn starch | 175.0 parts |
| | 200.0 parts |

Preparation:

The ingredients are intimately admixed with each other, and 200 mgm portions of the mixture are filled into gelatin capsules of suitable size. Each capsule contains 25 mgm of the hexamethylenediamine compound and is an oral dosage unit composition with effective β-adrenergic receptor blocking and hypotensive action.

EXAMPLE 19

Hypodermic Solution

The solution is compounded from the following ingredients:

| | |
|---|---|
| N,N'-bis-[2'-hydroxy-3'-(2''-cyano-phenoxy)-1'-propyl]-1,6-hexamethylenediamine . 2 HCl | 1.5 parts |
| Sodium salt of EDTA (ethylenediamine tetraacetic acid) | 0.2 parts |
| Distilled water  q.s.ad | 100.0 parts |

Preparation:

The active ingredient and the EDTA salt are dissolved in a sufficient amount of distilled water, and the solution is diluted with water to the indicated weight. The solution is filtered until free from suspended particles and filled into 1 cc-ampules under aseptic conditions. Finally, the ampules ae sterilized and sealed. Each ampule contains 15 mgm of the hexamethylenediamine compound, and the contents thereof are an injectable dosage unit composition with effective β-adrenergic receptor blocking and hypotensive action.

EXAMPLE 20

Coated Sustained-release Tablets

The tablet core composition is compounded from the following ingredients:

| | |
|---|---|
| N,N'-bis-[1'-(2''-cyano-5''-methyl-phenoxy)-2'-hydroxy-propyl-3']-1,2-ethylenediamine dihydrochloride | 25.0 parts |
| Carboxymethyl cellulose (CMC) | 295.0 parts |
| Stearic acid | 20.0 parts |
| Celluloseacetate phthalate (CAP) | 40.0 parts |
| | 380.0 parts |

Preparation:

The active ingredients, the CMC and the stearic acid are intimately mixed with each other, and the mixture is granulated in the conventional way, using a solution of the CAP in 200 mgm of an ethanol/ethylacetate mixture as the moistener. Then, the granulate is compressed into .380 mgm-tablet cores, which are subsequently coated with a mixture of sugar and polyvinylpyrrolidone. Each coated tablet contains 25 mgm of the ethylenediamine compound and is an oral dosage unit composition with effective β-adrenergic receptor blocking and hypotensive action.

Dosage unit compositions containing a compound of the present invention as an active ingredient may, in addition, also contain one or more other active ingredients with different pharmacological activities, such as coronary dilators, sympathomimetics and tranquilizers, as illustrated by the following examples.

EXAMPLE 21

Coated Sustained-release Tablets

The tablet core composition is compounded from the following ingredients:

| | |
|---|---|
| N,N'-bis-[2'-hydroxy-3'-(2''-cyano-phenoxy)-1'-propyl]-1,6-hexamethyl-enediamine . 2 HCl | 25.0 parts |
| Oxazepam | 20.0 parts |
| Carboxymethyl cellulose (CMC) | 295.0 parts |
| Stearic acid | 20.0 parts |
| Celluloseacetatephthalate (CAP) | 40.0 parts |
| | 400.0 parts |

Preparation:

The tablets are manufactured in a manner analogous to that described in Example 20. Each tablet contains 25 mgm of the hexamethylenediamine compound and 20 mgm of oxazepam, and is an oral dosage unit composition with effective β-adrenergic receptor blocking, hypotensive and tranquilizing action.

EXAMPLE 22

Tablets

The tablet composition is compounded from the following ingredients:

| | |
|---|---|
| N,N'-bis-[2'-hydroxy-3'-(4''-cyano-phenoxy)-1'-propyl]-1,6-hexamethyl-enediamine . 2 HCl | 35.0 parts |
| 2,6-bis-(diethanolamino)-4,8-di-piperidino-pyrimido-[5,4-d]-pyrimidine | 75.0 parts |
| Lactose | 164.0 parts |
| Corn starch | 194.0 parts |
| Colloidal silicic acid | 14.0 parts |
| Polyvinylpyrrolidone | 6.0 parts |
| Magnesium stearate | 2.0 parts |
| Soluble starch | 10.0 parts |
| | 500.0 parts |

Preparation:

The active ingredients are intimately admixed with the lactose, the corn starch, the colloidal silicic acid and the polyvinylpyrrolidone, and the mixture is granulated in the usual way, using an aqueous solution of the soluble starch as the moistener. The granulate is admixed with the magnesium stearate, and the composition is compressed into 500 mgm-tablets in a conventional tablet making machine. Each tablet contains 35 mgm of the hexamethylene diamine compound and 75 mgm of the pyrimidopyrimidine compound, and is an oral dosage unit composition with effective β-adrenergic receptor blocking, hypotensive and coronary dilating action.

Analogous results are obtained when any one of the other compounds embraced by formula I or a non-toxic acid addition salt thereof is substituted for the particular alkylenediamine derivative in Examples 17 through 22. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A β-adrenolytic and hypotensive pharmaceutical dosage unit composition consisting essentially of an inert pharmaceutical carrier and an effective β-adrenergic receptor blocking and hypotensive amount of a compound of the formula

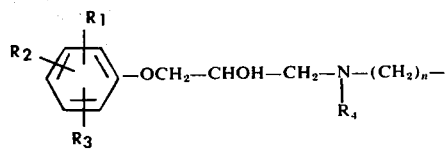

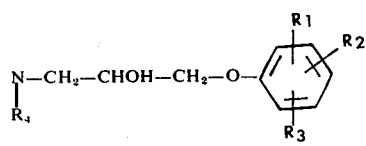

wherein $R_1$ is —$(CH_2)_x$—CN, where x is 0,1,2 or 3.

$R_2$ is hydrogen, halogen, alkyl of 1 to 5 carbon atoms, alkoxy of 1 to 5 carbon atoms, alkenyl of 2 to 5 carbon atoms or alkenyloxy of 2 to 5 carbon atoms;

$R_3$ is hydrogen, halogen, alkyl of 1 to 5 carbon atoms or alkoxy of 1 to 5 carbon atoms;

$R_2$ and $R_3$, together with each other and the carbon atoms to which they are attached, form a saturated or unsaturated carbocyclic ring of up to 6 carbon atoms;

$R_1$ is hydrogen, alkyl of 1 to 5 carbon atoms or aralkyl; and n is an integer from 1 to 10, inclusive; or a non-toxic, pharmacologically acceptable acid addition salt thereof.

2. A composition of claim 1, wherein said compound is one of the formula

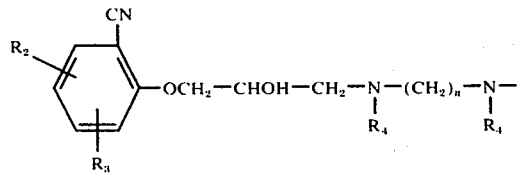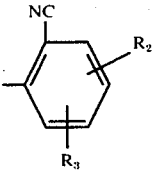

wherein $R_2$ is hydrogen, halogen, alkyl of 1 to 5 carbon atoms, alkoxy of 1 to 5 carbon atoms, alkenyl of 2 to 5 carbon atoms or alkenyloxy of 2 to 5 carbon atoms;

$R_3$ is hydrogen, halogen, alkyl of 1 to 5 carbon atoms or alkoxy of 1 to 5 carbon atoms;

$R_2$ and $R_3$, together with each other and the carbon atoms to which they are attached, form a saturated or unsaturated carbocyclic ring of up to 6 carbon atoms;

$R_4$ is hydrogen, alkyl of 1 to 5 carbon atoms or aralkyl; and n is an integer from 1 to 10, inclusive;

or a non-toxic, pharmacologically acceptable acid addition salt thereof.

3. A composition of claim 1, wherein said compound is N,N'-bis-[2'-hydroxy-3'-(2''-cyano-phenoxy)-1'-n-propyl]-1,6-hexamethylenediamine or a non-toxic, pharmacologically acceptable acid addition salt thereof.

4. The method of blocking the β-adrenergic receptors and lowering the blood pressure of a warm-blooded animal in need of such treatment, which comprises perorally or parenterally administering to said animal an effective β-adrenergic receptor blocking and hypotensive amount of a compound of the formula

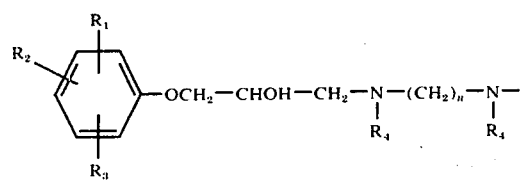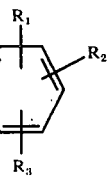

wherein $R_1$ is -$(CH_2)_x$-CN, where x is 0, 1, 2 or 3, $R_2$ is hydrogen, halogen, alkyl of 1 to 5 carbon atoms, alkoxy of 1 to 5 carbon atoms, alkenyl of 2 to 5 carbon atoms or alkenyloxy of 2 to 5 carbon atoms;

$R_3$ is hydrogen, alkyl of 1 to 5 carbon atoms or alkoxy of 1 to 5 carbon atoms;

$R_2$ and $R_3$, together with each other and the carbon atoms to which they are attached, form a saturated or unsaturated carbocyclic ring of up to 6 carbon atoms; and

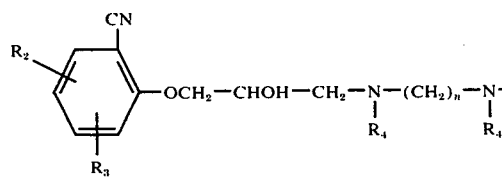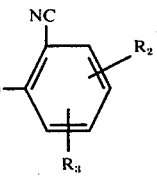

wherein $R_2$ is hydrogen, halogen, alkyl of 1 to 5 carbon atoms, alkenyl of 2 to 5 carbon atoms or alkenyloxy of 2 to 5 carbon atoms;

$R_3$ is hydrogen, halogen, alkyl of 1 to 5 carbon atoms or alkoxy of 1 to 5 carbon atoms;

$R_2$ and $R_3$, together with each other and the carbon atoms to which they are attached, form a saturated or unsaturated carbocyclic ring of up to 6 carbon atoms;

$R_4$ is hydrogen, alkyl of 1 to 5 carbon atoms or aralkyl; and n is an integer from 1 to 10, inclusive; or a non-toxic, pharmacologically acceptable acid addition salt thereof.

6. The method of claim 4, wherein said compound is N,N'-bis-[2'-hydroxy-3'-(2''-cyano-phenoxy)-1'-n-propyl]-1,6-hexamethylenediamine or a non-toxic, pharmacologically acceptable salt thereof.

* * * * *